(12) United States Patent
Neumiller et al.

(10) Patent No.: US 8,788,038 B2
(45) Date of Patent: Jul. 22, 2014

(54) EXTERNAL DEFIBRILLATOR WITH POWER AND BATTERY SHARING CAPABILITIES WITH A POD

(75) Inventors: James S. Neumiller, Redmond, WA (US); Thomas J. McGrath, Everett, WA (US); Rockland W. Nordness, Kirkland, WA (US); John C. Daynes, Redmond, WA (US)

(73) Assignee: Physio-Control, Inc., Redmond, WA (US)

(*) Notice: Subject to any disclaimer, the term of this patent is extended or adjusted under 35 U.S.C. 154(b) by 1485 days.

(21) Appl. No.: 10/583,175

(22) PCT Filed: Dec. 17, 2004

(86) PCT No.: PCT/US2004/042376
§ 371 (c)(1),
(2), (4) Date: Nov. 1, 2007

(87) PCT Pub. No.: WO2005/058416
PCT Pub. Date: Jun. 30, 2005

(65) Prior Publication Data
US 2008/0183229 A1     Jul. 31, 2008

Related U.S. Application Data (60) Provisional application No. 60/530,151, filed on Dec. 17, 2003.

(51) Int. Cl.
  *A61N 1/00* (2006.01)
  *A61B 5/02* (2006.01)
  *A61B 5/04* (2006.01)
(52) U.S. Cl.
  USPC ............... 607/5; 607/4; 607/142; 600/508; 600/522; 600/523

(58) Field of Classification Search
USPC .............. 607/142, 4, 5; 600/508, 522, 523
See application file for complete search history.

(56) References Cited

U.S. PATENT DOCUMENTS 3,724,455 A     4/1973 Unger
3,865,101 A *   2/1975 Saper et al. .................. 600/508
(Continued)

FOREIGN PATENT DOCUMENTS

EP     1228782 A1     8/2002
EP     1250944 A2    10/2002
(Continued)

OTHER PUBLICATIONS

Restriction Requirement from U.S. Appl. No. 11/256,275, mailed Feb. 5, 2008, 7 pp.
(Continued)

*Primary Examiner* — Niketa Patel
*Assistant Examiner* — William Levicky
(74) *Attorney, Agent, or Firm* — Marger, Johnson & McCollom, P.C.

(57) ABSTRACT

A modular external defibrillator system in embodiments of the teachings may include one or more of the following features: (a) a base containing a defibrillator module to deliver a defibrillation shock to a patient, (b) a patient parameter monitoring pod connectable to a patient via patient lead cables to collect patient data, the patient data including at least one patient vital sign, (c) a power supply sharing link between the base and the pod, the pod receiving power from the base via the power sharing link, the pod being operable to collect patient data without receiving power from the base, and (d) an external battery charger, the battery charger interrogating the batteries to determine battery information used for battery charging, the battery information including at least one of charging voltage, charging current, and charge time.

15 Claims, 11 Drawing Sheets

(56) References Cited

U.S. PATENT DOCUMENTS

| | | | |
|---|---|---|---|
| 4,096,856 A * | 6/1978 | Smith et al. | 607/5 |
| 5,012,411 A * | 4/1991 | Policastro et al. | 600/485 |
| 5,078,134 A * | 1/1992 | Heilman et al. | 607/4 |
| 5,105,821 A | 4/1992 | Reyes | |
| 5,470,343 A * | 11/1995 | Fincke et al. | 607/5 |
| 5,593,426 A | 1/1997 | Morgan et al. | |
| 5,685,314 A * | 11/1997 | Geheb et al. | 600/513 |
| 6,134,468 A | 10/2000 | Morgan et al. | |
| 6,141,584 A | 10/2000 | Rockwell et al. | |
| 6,183,417 B1 | 2/2001 | Geheb et al. | |
| 6,223,077 B1 * | 4/2001 | Schweizer et al. | 607/5 |
| 6,275,737 B1 * | 8/2001 | Mann | 607/61 |
| 6,441,747 B1 | 8/2002 | Khair et al. | |
| 6,978,181 B1 | 12/2005 | Snell | |
| 7,110,825 B2 * | 9/2006 | Vaynberg et al. | 607/63 |
| 2002/0116028 A1 | 8/2002 | Greatbatch et al. | |
| 2002/0116029 A1 | 8/2002 | Miller et al. | |
| 2002/0116033 A1 | 8/2002 | Greatbatch et al. | |
| 2002/0116034 A1 | 8/2002 | Miller et al. | |
| 2002/0128689 A1 | 9/2002 | Connelly et al. | |
| 2002/0128691 A1 | 9/2002 | Connelly | |
| 2002/0133086 A1 | 9/2002 | Connelly et al. | |
| 2002/0133199 A1 | 9/2002 | MacDonald et al. | |
| 2002/0133200 A1 | 9/2002 | Weiner et al. | |
| 2002/0133201 A1 | 9/2002 | Connelly et al. | |
| 2002/0133202 A1 | 9/2002 | Connelly et al. | |
| 2002/0133208 A1 | 9/2002 | Connelly et al. | |
| 2002/0133211 A1 | 9/2002 | Weiner et al. | |
| 2002/0133216 A1 | 9/2002 | Connelly et al. | |
| 2002/0138102 A1 | 9/2002 | Weiner et al. | |
| 2002/0138107 A1 | 9/2002 | Weiner et al. | |
| 2002/0138108 A1 | 9/2002 | Weiner et al. | |
| 2002/0138110 A1 | 9/2002 | Connelly et al. | |
| 2002/0138112 A1 | 9/2002 | Connelly et al. | |
| 2002/0138113 A1 | 9/2002 | Connelly et al. | |
| 2002/0138124 A1 | 9/2002 | Helfer et al. | |
| 2002/0143258 A1 | 10/2002 | Weiner et al. | |
| 2002/0147470 A1 | 10/2002 | Weiner et al. | |
| 2002/0183796 A1 | 12/2002 | Connelly | |
| 2002/0198569 A1 | 12/2002 | Foster et al. | |
| 2003/0028219 A1 | 2/2003 | Powers et al. | |
| 2003/0088275 A1 * | 5/2003 | Palmer et al. | 607/5 |
| 2004/0049233 A1 | 3/2004 | Edwards | |
| 2004/0162586 A1 | 8/2004 | Covey et al. | |
| 2005/0124866 A1 * | 6/2005 | Elaz et al. | 600/301 |
| 2006/0142808 A1 | 6/2006 | Pearce et al. | |
| 2008/0077185 A1 | 3/2008 | Pearce et al. | |
| 2008/0221397 A1 | 9/2008 | McMahon et al. | |

FOREIGN PATENT DOCUMENTS

| | | |
|---|---|---|
| WO | 0166182 A1 | 9/2001 |
| WO | 03009895 A1 | 2/2003 |

OTHER PUBLICATIONS

Response to Restriction Requirement mailed Feb. 5, 2008, from U.S. Appl. No. 11/256,275, filed May 14, 2008, 1 pg.
Office Action from U.S. Appl. No. 11/256,275, mailed Jun. 9, 2008, 6 pp.
Response to Office Action mailed Jun. 9, 2008, from U.S. Appl. No. 11/256,275, filed Oct. 8, 2008, 9 pp.
Office Action from U.S. Appl. No. 11/256,275, mailed Jan. 6, 2009, 8 pp.
Response to Office Action mailed Jan. 6, 2009, from U.S. Appl. No. 11/256,275, filed Apr. 3, 2009, 7 pp.
Office Action from U.S. Appl. No. 11/256,275, mailed Jun. 9, 2009, 11 pp.
Response to Office Action mailed Jun. 9, 2009, from U.S. Appl. No. 11/256,275, filed Sep. 9, 2009, 9 pp.
International Search Report and Written Opinion from international application No. PCT/US2004/042376, mailed Mar. 24, 2005, 7 pp.
International Preliminary Report on Patentability from international application No. PCT/US2004/042376, issued Jun. 20, 2006, 6 pp.
International Search Report and Written Opinion from international application No. PCT/US2004/042792, mailed Jul. 20, 2005, 12 pp.
International Preliminary Report on Patentability from international application No. PCT/US2004/042792, issued Jun. 20, 2006, 8 pp.
International Search Report and Written Opinion from international application No. PCT/US2004/012421, mailed Sep. 13, 2004, 7 pp.
International Preliminary Report on Patentability from international application No. PCT/US2004/012421, issued Oct. 28, 2005, 6 pp.
Non Final Office Action for corresponding U.S. Appl. No. 11/256,275 dated Feb. 3, 2010, (14 pgs.).
Response to Non Final Office Action for corresponding U.S. Appl. No. 11/256,275 dated Apr. 20, 2010 (12 pgs.).
Office Action from U.S. Appl. No. 10/583,209, dated Mar. 16, 2010, 11 pp.
Response to Office Action dated Mar. 16, 2010, from U.S. Appl. No. 10/583,209, filed Jun. 16, 2010, 17 pp.
Office Action for U.S. Appl. No. 10/583,209 dated Oct. 19, 2010, (9 pp).
Response to Office Action for U.S. Appl. No. 10/583,209 dated Dec. 20, 2010 (8 pp).
Office Action from U.S. Appl. No. 11/256,275 dated Feb. 3, 2011 (10 pp).

* cited by examiner

EXTERNAL DEFIBRILLATOR WITH POWER AND BATTERY SHARING CAPABILITIES WITH A POD

CROSS REFERENCE

This application is a National Stage Entry of International PCT Application No. US2004/04376, titled "An External Defibrillator with Power and Battery Sharing Capabilities with a Pod" filed on Dec. 17, 2004, which claims priority to International PCT Application No. US2004/012421 titled "Defibrillator/Monitor System Having a Pod with Leads Capable of Wirelessly Communicating" filed on Apr. 22, 2004, which claims benefit of U.S. Provisional Application Ser. No. 60/464,860 titled "System of POD with leads and defibrillator monitor communicating wirelessly with each other," and to U.S. Provisional Application Ser. No. 60/530,151 titled "Defibrillator/Monitor System Having a Pod with Leads Capable of Wirelessly Communicating" filed on Dec. 17, 2003, which are both hereby incorporated by reference in their entirety.

This disclosure is related to the following applications entitled "DEFIBRILLATOR PATIENT MONITORING POD" U.S. Publication No. 2008/0221397 filed 17 Dec. 2004, and U.S. Pat. No. 7,957,798 entitled "DEFIBRILLATOR/MONITOR SYSTEM HAVING A POD WITH LEADS CAPABLE OF WIRELESSLY COMMUNICATING" filed 17 Dec. 2004 and issued 6 Jun. 2011, which are hereby incorporated by reference in their entirety and not admitted as prior art with respect to the present disclosure by its mention in this section.

TECHNICAL FIELD

The invention relates to medical devices, and in particular, to defibrillation/monitor systems having a detachable pod with leads.

BACKGROUND

Each day thousands of Americans are victims of cardiac emergencies. Cardiac emergencies typically strike without warning, oftentimes striking people with no history of heart disease. The most common cardiac emergency is sudden cardiac arrest ("SCA"). It is estimated more than 1000 people per day are victims of SCA in the United States alone.

SCA occurs when the heart stops pumping blood. Usually SCA is due to abnormal electrical activity in the heart, resulting in an abnormal rhythm (arrhythmia). One such abnormal rhythm, ventricular fibrillation (VF), is caused by abnormal and very fast electrical activity in the heart. During VF the heart cannot pump blood effectively. Because blood may no longer be pumping effectively during VF, the chances of surviving decreases with time after the onset of the emergency. Brain damage can occur after the brain is deprived of oxygen for four to six minutes.

Applying an electric shock to the patient's heart through the use of a defibrillator treats VF. The shock clears the heart of the abnormal electrical activity (in a process called "defibrillation") by depolarizing a critical mass of myocardial cells to allow spontaneous organized myocardial depolarization to resume.

Cardiac arrest is a life-threatening medical condition that may be treated with external defibrillation. External defibrillation includes applying electrodes to the patient's chest and delivering an electric shock to the patient to depolarize the patient's heart and restore normal sinus rhythm. The chance a patient's heart can be successfully defibrillated increases significantly if a defibrillation pulse is applied quickly.

In a scenario where a paramedic is responding to an emergency call with a non-specific patient condition, for example, there has been a car accident. The paramedic will typically carry his or her own defibrillator/monitor, a gurney, and drug box, and other supplies considered essential. If, perhaps, the car has driven off an embankment, the paramedic will have a long distance to run with all this equipment. This slows the response time to a call where someone may be bleeding to death. Smaller lighter equipment is always demanded by paramedics to save them time and effort, and allow them to get to the scene earlier. For just this reason, some paramedics will opt to carry only an AED (Automatic External Defibrillator) to the scene, and move the patient into the ambulance as quickly as possible, where other, more advanced monitoring equipment is available. In some countries, this approach has been incorporated into standard operating protocols, where the ambulance carries both ALS (advanced life support) equipment (which typically would include a multi-parameter monitor and defibrillator) and an AED. This approach, while effectively giving the user the choice of equipment to carry, forces the paramedic to learn two different defibrillators. The approach also forces the paramedics to possibly transfer the patient from one machine to the other once in the ambulance. It also adds costs to the ambulance service and potentially causes lost data between the two defibrillators for critical minutes, which may negatively impact the ability of EP Lab (Electro-Physiology Lab) doctors to determine the original cardiac condition.

Previous attempts to address the issue of product weight have done so by creating a manual defibrillator that separates from a patient monitor, or an AED, which separates from a single-channel patient monitor, or a manual defibrillator/pacemaker that separates from a 12-lead ECG monitor. These products suffer from limitations by the present standards, such as: limited capture of patient data, limited ability to monitor all necessary patient vital signs, and possible unreliability due to the nature of the electrical contacts between the two devices (e.g., dirt, mud, and damage to the case which could affect alignment of electrical contacts, thus preventing full functionality of the devices when mated).

Another problem arises when hospital personnel want to charge the batteries of the defibrillator/monitor, but don't want to have to place the unit in a docking station in order to charge the batteries. There also arises the issue of patient confidentiality, such as recently raised by the Federal HIPAA (Health Insurance Portability and Accountability Act) regulations, when identical looking patient monitors are accidentally swapped by users.

SUMMARY

A modular external defibrillator system in embodiments of the teachings may include one or more of the following features: (a) a base containing a defibrillator module to deliver a defibrillation shock to a patient, (b) a patient parameter monitoring pod connectable to a patient via patient lead cables to collect patient data, the patient data including at least one patient vital sign, (c) a power supply sharing link between the base and the pod, the pod receiving power from the base via the power sharing link, the pod being operable to collect patient data without receiving power from the base, and (d) an external battery charger, the battery charger interrogating the batteries to determine battery information used for battery charging, the battery information including at least one of charging voltage, charging current, and charge time.

A modular external defibrillator system in embodiments of the teachings may include one or more of the following features: (a) a base containing a defibrillator module to deliver a defibrillation shock to a patient, (b) a patient parameter monitoring pod connectable to a patient via patient lead cables to collect patient data, the patient data including at least one patient vital sign, and (c) a power communications link between the base and the pod, the pod receiving power-on command signaling from the base via the power communications link, the pod being operable to power-on to a condition where the pod may collect patient data after receiving the power-on command signaling, the pod being operable to power-on without receiving the power-on command signaling.

A modular external defibrillator system in embodiments of the teachings may include one or more of the following features: (a) a base containing a defibrillator module to deliver a defibrillation shock to a patient, (b) a patient parameter monitoring pod connectable to a patient via patient lead cables to collect patient data, the patient data including at least one patient vital sign, the pod containing a battery operable to supply power for pod operation, (c) a battery power communications link between the base and the pod, the battery power communications link transferring pod battery information, the battery information including at least one of battery usage, battery charge status, battery charging information.

DETAILED DESCRIPTION

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

Figure 1:
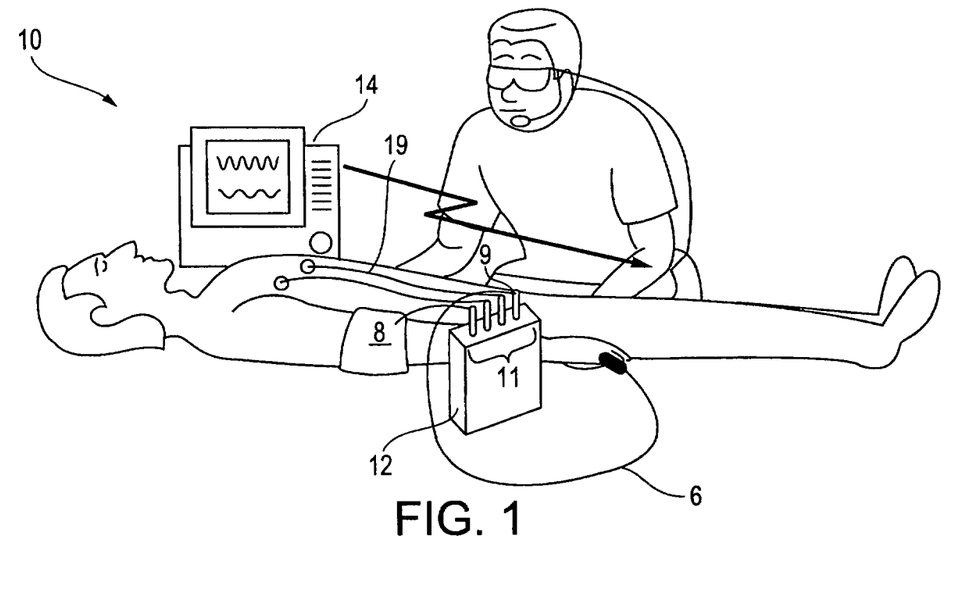
FIG. 1 is a pictorial representation of an external defibrillator having a patient module with a defibrillator/monitor in an embodiment of the present teachings.

With reference to FIG. 1, a pictorial representation of an external defibrillator having a patient module with a defibrillator/monitor in an embodiment of the present teachings is shown. External defibrillator 10 is comprised of two components patient module (pod) 12 and defibrillator/monitor (base) 14, which communicate patient data (e.g., vital signs) and share common replaceable battery technology. Pod 12 generally rests within base 14, generally in the back of base 14. The operator, during an emergency, has the option of carrying base 14 with pod 12 attached or simply carrying pod 12 to the emergency site. Since pod 12 is smaller and lighter than base 14, generally it will be easier for the operator to simply carry pod 12. By carrying pod 12, the operator is free to carry more ALS equipment and not be slowed by the heavier and more awkward base 14.

Pod 12 connects to a patient via several leads 6, 8, 9, 11, and 19 in order to measure the patient's vital signs. Pod 12 communicates the patient's vital signs either wirelessly or via an electrical connection to defibrillator monitor 14. The patient data or vital signs collected may include 3, 4, and 5 lead ECG readings, 12 lead ECG readings, non-invasive blood pressure (NIBP), pulse oximeter data, capnography data, invasive blood pressure, body temperature, $CO_2$ levels, and additional patient monitoring functions. Additionally, pod 12 may include a small display 82 (shown in FIG. 4) replicating some or all of the information such as waveforms, numerical data, and vital signs being transmitted to base 14.

Base 14 includes a therapy module 56 (FIG. 3) and therapy cables. Therapy module 56 has the capability to provide therapeutic functions such as pacing, defibrillation, or synchronous cardioversion without attaching another monitor/defibrillator to the patient. The therapy cables typically include patient paddles or electrodes that attach between the patient and base 14 in order to deliver the therapy to the patient. Since pod 12 connects to the patient and transmits vital signs to base 14, then base 14 need not also have patient monitoring cables. Accordingly, paramedic mobility and ease of use are greatly increased. Therapy module 56 in base 14 may be configurable in either an ALS mode or an AED mode. The ALS mode includes a multi-parameter monitoring capability and all of the defibrillator therapy delivery capability. Additionally base unit 14 may be just an AED.

Figure 2:
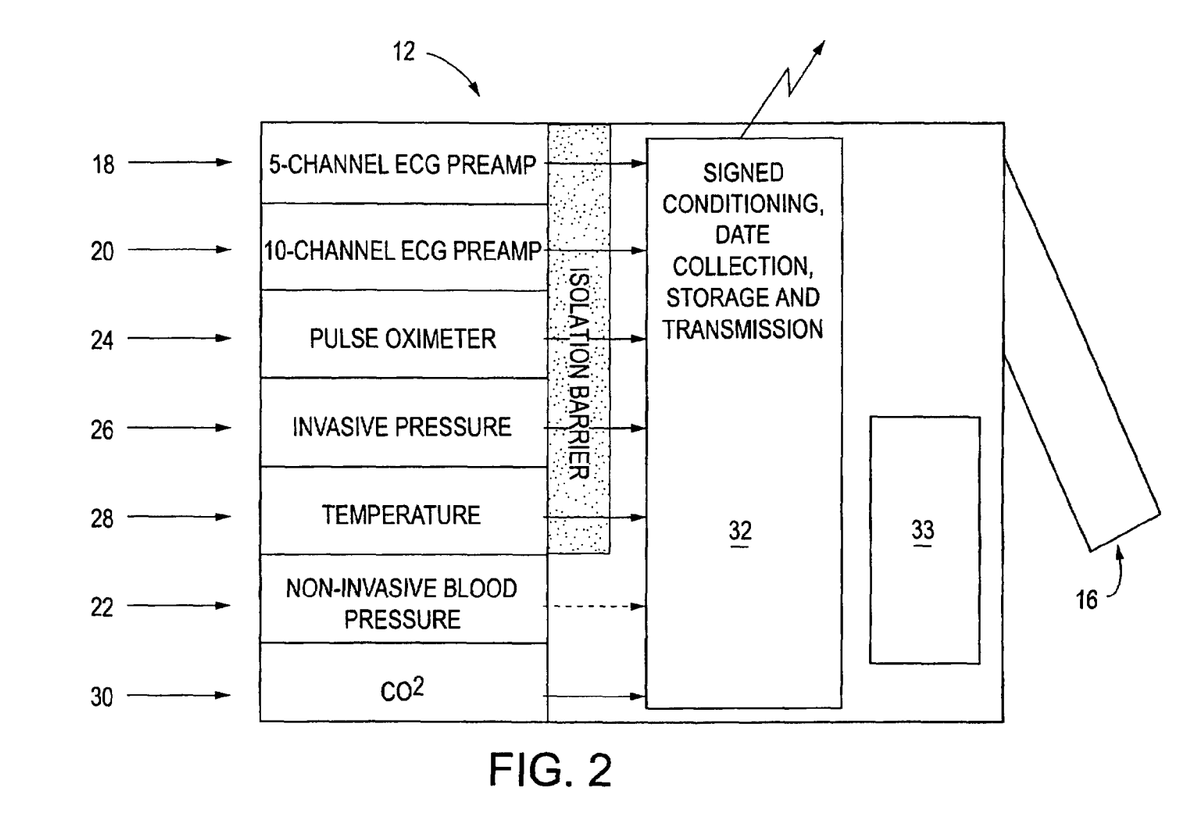
FIG. 2 is an upper level pictorial representation of a patient module pod in an embodiment of the present teachings.
Figure 3:
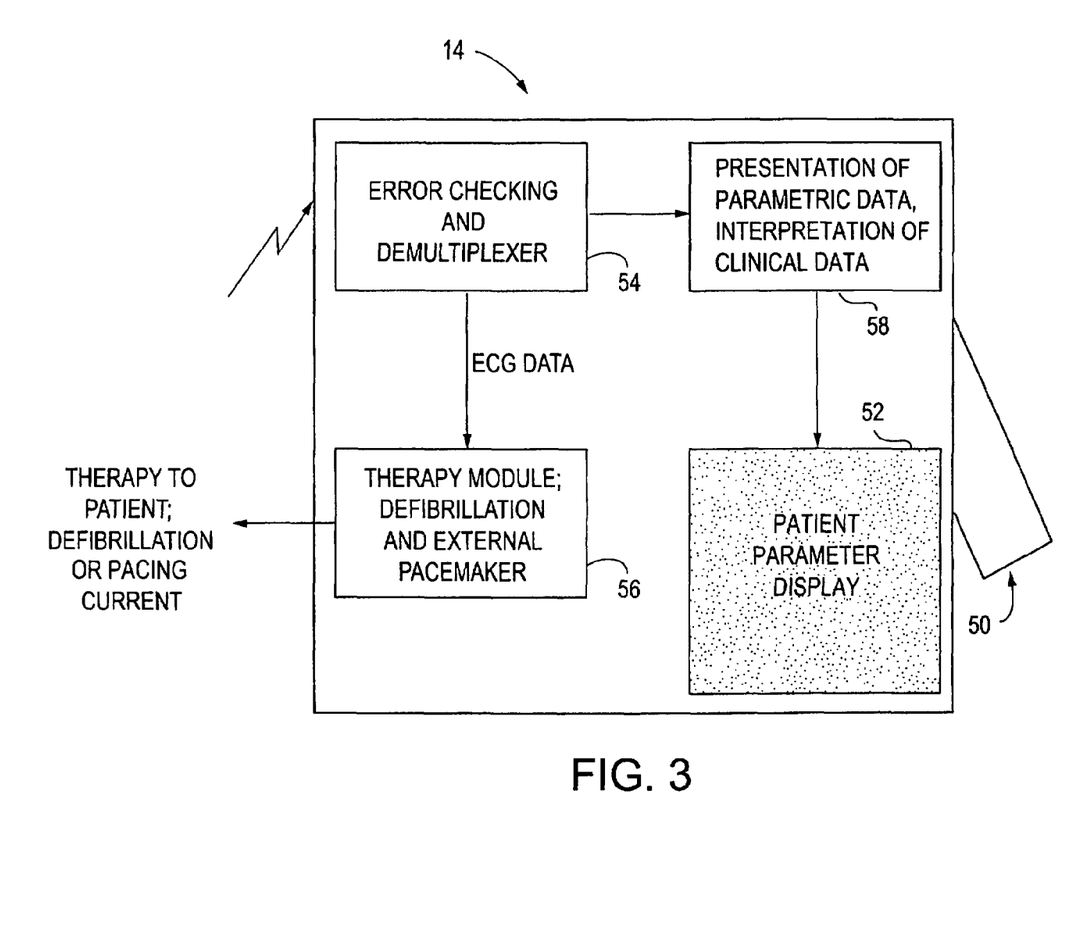
FIG. 3 is an upper level pictorial representation of a defibrillator/monitor base in an embodiment of the present teachings.

With reference to FIG. 2, an upper level pictorial representation of a patient module in an embodiment of the present teachings is shown. Generally, pod 12 uses replaceable or rechargeable batteries 16 for power and comprises any combination of the following features: 3, 4, and 5 lead ECG inputs 18, 12 lead ECG inputs 20, non-invasive blood pressure (NIBP) input 22, pulse oximeter input 24, capnography input (not shown), invasive blood pressure input 26, temperature input 28, $CO_2$ input 30, additional patient monitoring functions, transceiver 32 to transmit any or all real time patient data to base 14. Transceiver 32 can be a wireless BlueTooth module commercially available from TDK, however, transceiver 32 can be any transceiver such as WiFi (802.11), Wireless WAN (CDMA, GSM, GPRS, UTMS, etc.), or a wired Fire-Wire (IEEE 1394) without departing from the spirit of the present teachings. Additionally, pod 12 may include a patient parameter display 33 replicating some or all of the information such as waveforms, numerical data, and vital signs being transmitted to base 14. Additionally, pod 12 includes some means by which it can be attached to base 14 for the purpose of carrying base 14 to an emergency scene as is discussed in P.C.T. Application Serial No. US04/12421. Additionally, pod 12 may have a feature allowing it to be easily secured to a gurney or hospital bed as is discussed in a patent application entitled "DEFIBRILLATOR PATIENT MONITORING POD" U.S. Publication No. 2008/0221397 filed 17 Dec. 2004 herein incorporated by reference in its entirety. With reference to FIG. 3, an upper level pictorial representation of a defibrillator/monitor in an embodiment of the present teachings is shown. Base 14 uses a replaceable or rechargeable battery 50 for power. Batteries 16 and 50 are generally similar in battery chemistry, electrical, and mechanical features to permit the interchangeability between batteries 16 and 50. Batteries 16 and 50 can be a Li Ion battery providing 16 volts and 3.8 amps, however, most any type of battery can be used without departing from the spirit of the invention. Additionally, base 14 comprises a display 52 sufficient to show current and historical patient data, a transceiver (similar to transceiver 32 [not shown]) to send acquired patient data onto a receiving station or third party data receiver, a module 56 to synchronize shocks and pacing pulses to the patient's intrinsic rhythm from data acquired by a pod 12, an error checking and de-multiplexing module 54 receiving and processing data received from pod 12, and a data interpretation module 58 which analyzes data acquired by pod 12 and makes certain interpretive statements on the patient's cardiac or respiratory condition, displays vital sign trends, and provides additional functions found in ALS monitoring products.

Figure 4:
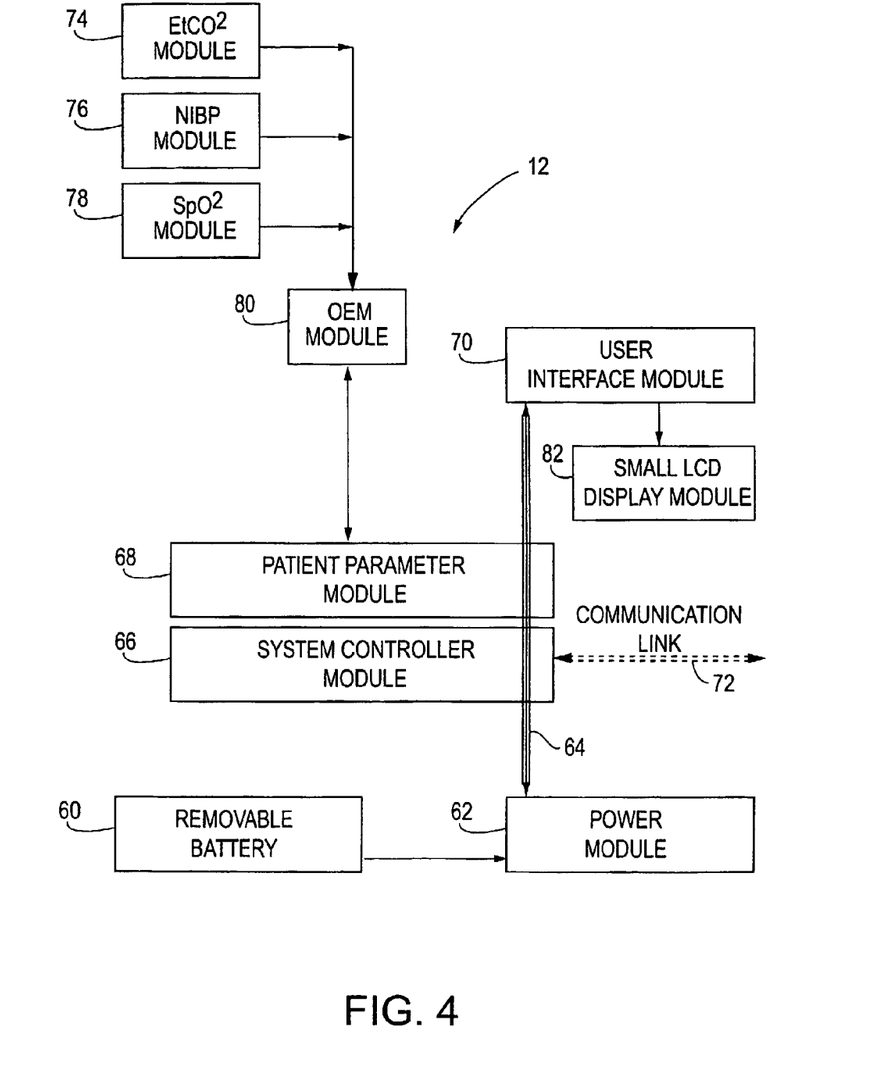
FIG. 4 is a schematic view of a patient module pod in an embodiment of the present teachings.

With reference to FIG. 4, a schematic view of a patient monitor in an embodiment of the present teachings is shown. As discussed above, pod 12 can be powered from a removable/rechargeable battery 60. Power module 62 processes the incoming power into appropriate power levels for each of the internal components. Power module 62 routes the pod's power supply through main power and data bus 64 to system controller module 66, patient parameter module 68, and operator interface module 70. As discussed above, pod 12 can be used wirelessly, however, it is helpful if pod 12 is directly connected through a tethered cable 46 or through attachment to a connector to utilize the speed of data bus 64.

Figure 9:
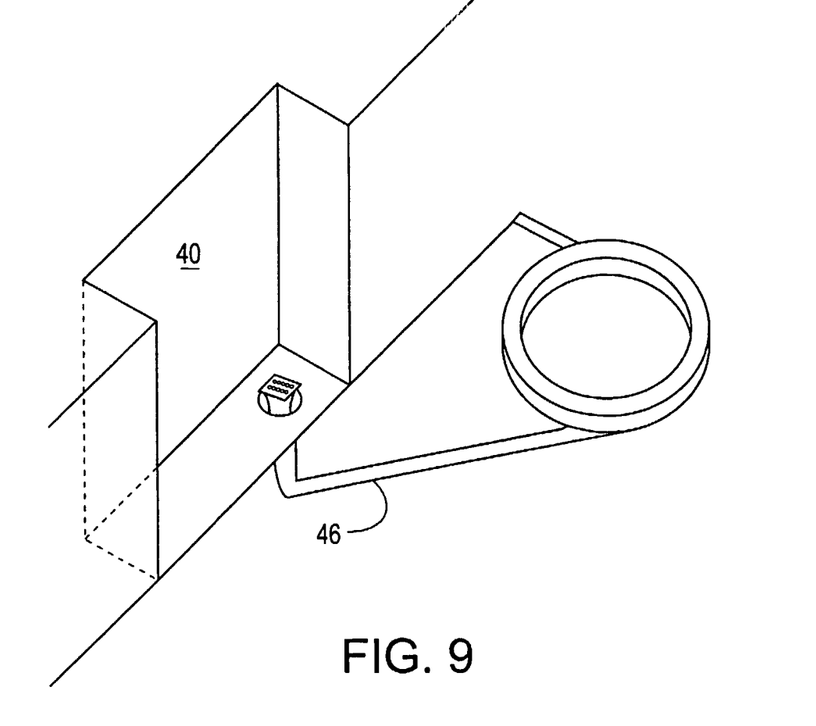
FIG. 9 is a pictorial representation of a mating assembly having a tethered connector in an embodiment of the present teachings.
Figure 10:
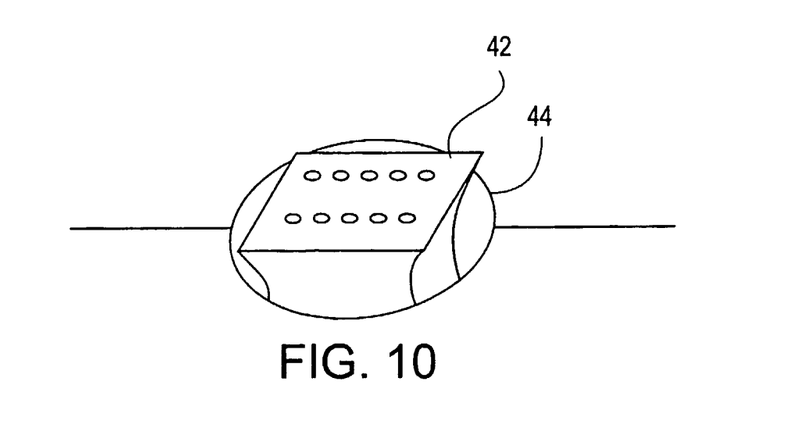
FIG. 10 is a pictorial representation of a mating assembly having a tethered connector in an embodiment of the present teachings.

With reference to FIGS. 9 and 10, a pictorial representation of a mating assembly having a tethered connector in an embodiment of the present teachings is shown. In this embodiment, a pod similar to 12 rests within slot 40 and connects to base-to-pod connector 42, which allows base 14 and a pod to communicate with each other. Base-to-pod connector 42 rests freely within connector cavity 44, which allows connector cable 46 to retractably exit and enter base 14. Tethered cable 46 allows a pod to mate with and rest within base 14 or mate with base 14 when not docked within slot 40. It is sometimes helpful that base 14 communicate with a pod through tethered cable 46 since communications through a direct connection is generally faster. This is the case in the present embodiment as base 14 is equipped with a high-speed bus, such as a USB bus, which provides quick communication of information between a pod and base 14. Base 14 is also able to automatically detect when tethered cable 46 is plugged in so direct communications can be established immediately. A direct communication between a pod and base 14 can be established. This automatic establishment of direct communication between a pod and base 14 includes when a pod is docked within base 14 and a connection is made between a pod and base 14 through connector 42.

Generally base 14 and a pod communicate wirelessly to assist in preventing the tangling of cables, which can occur between a patient and base 14, particularly when transporting patients. Tethered cable 46 provides a system for use when the wireless link between pod 12 and base 14 fails for whatever reason or when precise signal synchronization demands a wired connection. Tethered cable 46 also provides the added advantage in that the user cannot lose cable 46 because it is tethered to base 14. Wireless links can impose a delay in communication between a pod and base 14 longer than may be experienced with a cable. When communications between base 14 and a pod require a faster response time (such as application of synchronous cardioversion or pacing where information from a pod must be transmitted to base 14), the user is advised of the need to plug cable 46 into the pod or attaché pod 12 to base 14. The user is provided a user interface message to inform them of the need to attach cable 46.

With reference again to FIG. 4, system controller module 66 controls interaction of all the pod's modules through data bus 64 and interaction with base 14 through a wired connection, such as tethered cable 46 or wireless (e.g., IrDA, RF, etc.) communication link 72 which would be transmitted by transceiver 32. System controller module 66 has the ability to encrypt data communicated over the wireless links to meet HIPAA requirements for the protection of patient data. There can be a single encryption key for all bases and pods. However, it is contemplated there could be a user defined encryption key that can be set at the base by an operator. Patient parameter module 68 monitors functions such as invasive blood pressure, patient's temperature, and inputs from the pod leads. Module 68 further collects inputs from EtCO2 module 74, NIBP module 76, and SpO2 module 78 through OEM module 80. Patient parameter module 68 takes all of these inputs and processes them for display and can route only a limited number of inputs to small LCD display module 82 through operator interface module 70. Patient Parameter Module 68 also has the ability to perform interpretation of clinical data and can make certain interpretive statements about the patient's condition (e.g., cardiac or respiratory health). Power module 62 provides on/off control to the pod, utilizing the removable battery 60 as the power source. Operator Interface module 70 allows the operator to primarily interact with pod 12; however, it is contemplated that operator could use the module 70 to interact with base 14 as well.

Figure 5:
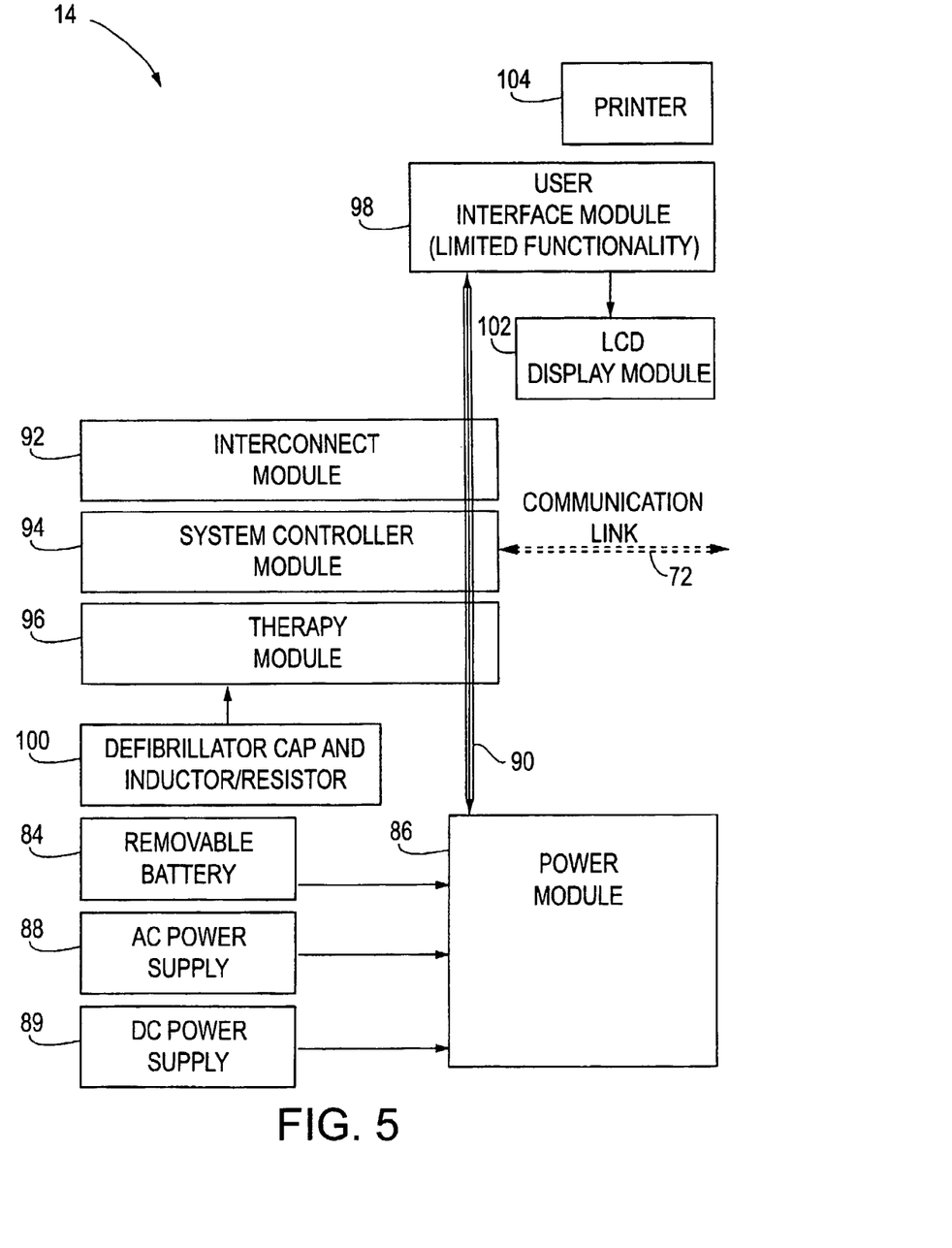
FIG. 5 is a schematic view of a defibrillator/monitor base in an embodiment of the present teachings.

With reference to FIG. 5, a schematic view of a defibrillator/monitor in an embodiment of the present teachings is shown. Base 14 is powered by a removable/rechargeable battery 84, which provides power to power module 86. Alternatively, base 14 could be powered by AC power supply 88 or DC power supply 93. Power module 86 processes the incoming power into appropriate powered levels for each of the internal components. Power module 86 also routes the base's power supply through main power and data bus 90 to interconnect module 92, system controller module 94, therapy module 96, and operator interface module 98. Interconnect module 92 is utilized to detect how pod 12 is connected to base 14 (wirelessly, docked, or tethered cable). When pod 12 is docked or tethered to base 14, interconnect module 92 can route the power provided from power module 86 to the pod 12. Additionally interconnect module 92, in conjunction with system controller 94, store all of the information about the associations that have been established between the base 12 and pod 14. Similar to system controller module 66 (in FIG. 4), system controller module 94 controls all interaction of all of the base's modules through data bus 90 and interaction with pod 12 through wired or wireless connection communication link 72 or through data bus 90 if pod 12 is connected to base 14. System controller module 94 and interconnect module 92 have the ability to encrypt data communicated over the wireless links to meet HIPAA requirements for the protection of patient data. Therapy module 96 synchronizes shocks and pacing pulses to the patient's intrinsic rhythm from data acquired from pod 12. Module 96 administers shocks from voltages via the defibrillation cap 100 and, in turn, administers pacing pulses to a patient. Operator interface module 98 allows the operator to primarily interact with base 14; however, it is contemplated that the operator could use the module 98 to interact with pod 12 as well. For example, patient demographic data (e.g., age, sex, height, weight) could be entered at the base 14, and communicated to the pod 12 for use in interpretive algorithms performed in system controller 66 within pod 12. LCD module 102 allows the operator to view a patient's monitored parameters. Finally, the operator has the option to print out patient information on a printer 104 (e.g., a 100 mm strip chart printer).

Figure 6:
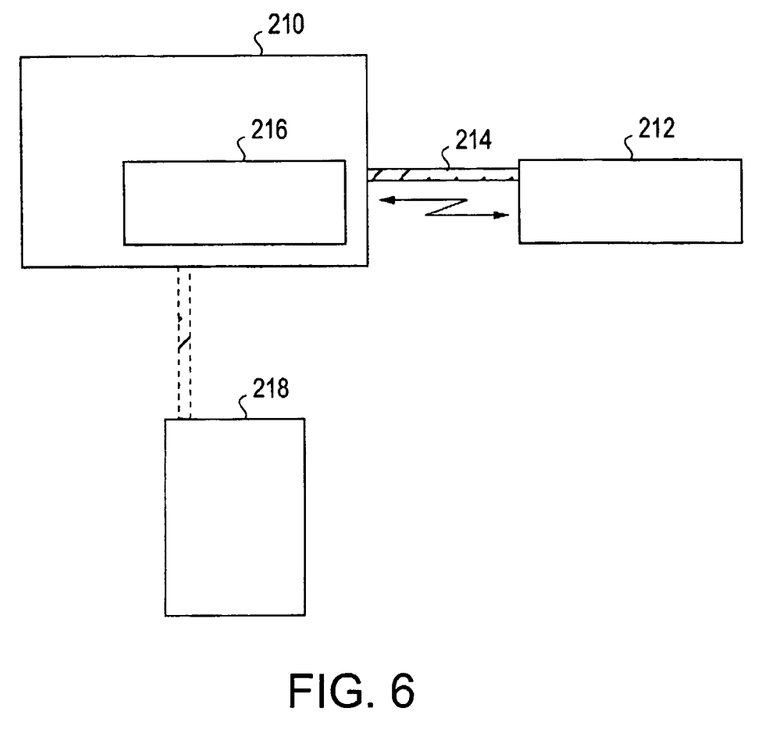
FIG. 6 is a pictorial display of a patient module pod and a defibrillator/monitor base in a power sharing embodiment of the present invention.
Figure 7:
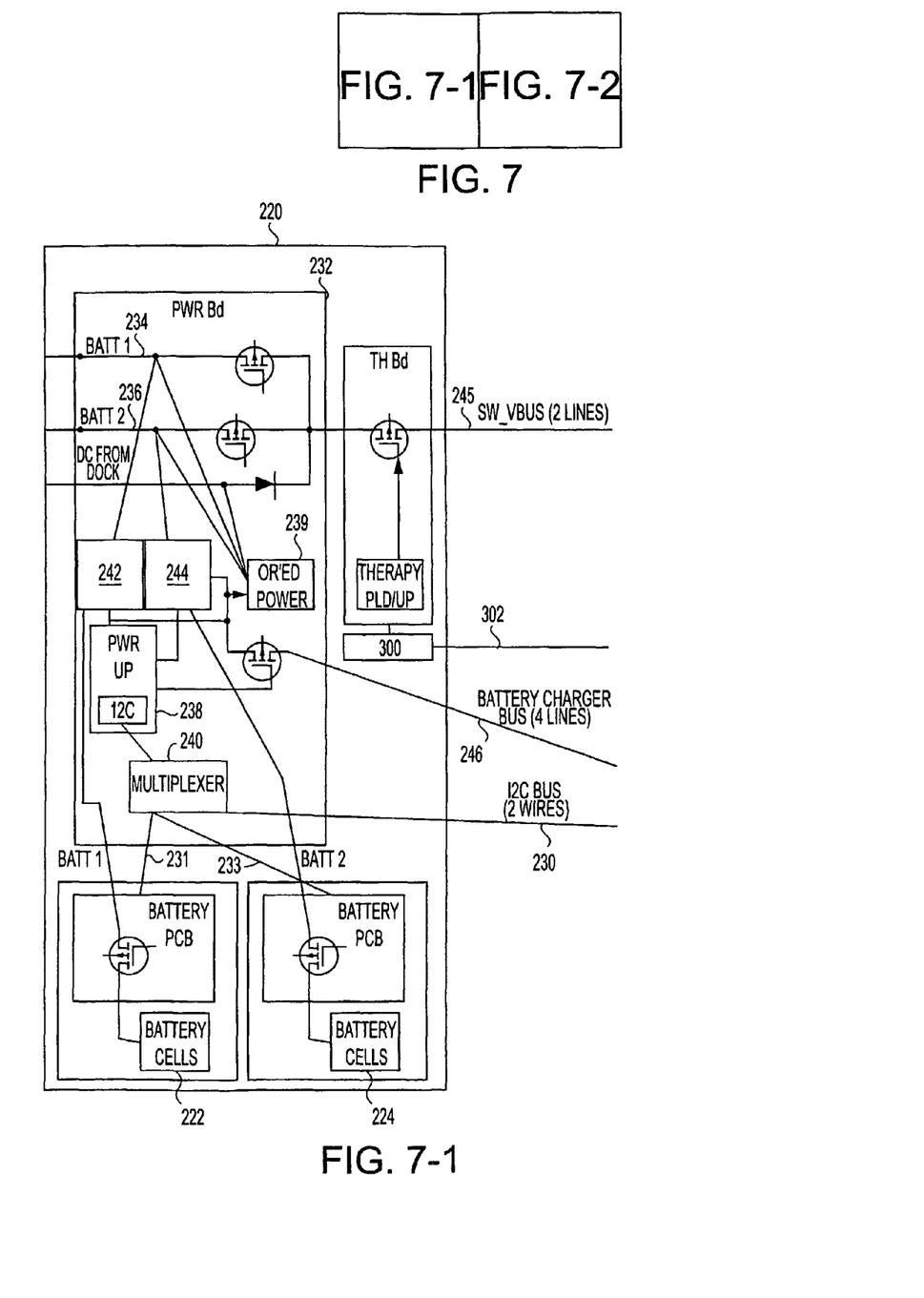
FIG. 7 is a schematic view of a defibrillator/monitor base providing battery charging control of a patient module pod in an embodiment of the present invention.
Figure 8:
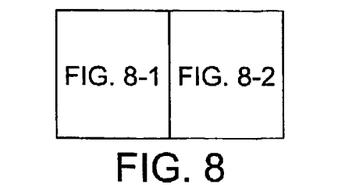
FIG. 8 is a schematic view of a defibrillator/monitor base battery charging scheme in an embodiment of the present invention.

With reference to FIGS. 6 and 7, a display of a patient module and a defibrillator/monitor in a power-sharing embodiment of the present invention is shown. In the present embodiment, and as stated above, both pod 212 and base 210 have separate but interchangeable batteries (not shown). In a preferred embodiment base 210 has 2 batteries each of which is interchangeable with the pod's battery. Generally, the extra battery is needed to provide the necessary energy for defibrillation therapy as well as providing energy to pod 212 when necessary as will be discussed in more detail below. Generally, upon power up both base 210 and pod 212 power up on their respective batteries. Moreover, pod 212 will remain on its own battery power in order to conserve the base's battery so base 210 will be able to provide defibrillation therapy to a patient when it is needed. In this situation the pod does not draw any power from power bus 245. As discussed above, base 210 will quickly establish communications with pod 212 to determine if pod 212 is docked in station 216, tethered by cable 214, or is remote using wireless communications as is discussed in U.S. Pat. No. 7,957,798 entitled "DEFIBRILLATOR/MONITOR SYSTEM HAVING A POD WITH LEADS CAPABLE OF WIRELESSLY COMMUNICATING" filed 17 Dec. 2004 and issued 6 Jun. 2011 herein incorporated by reference in its entirety. If pod 212 is docked or tethered, base 210 may communicate to pod 212 whether base 210 is connected to an external power source 218, detectable by the presence of power on power bus 287 (FIG. 8). External power source 218 could be an AC or DC power source or even an AC or DC power supply. If base 210 is connected to external power source 218, the base would communicate to pod 212 to quit using its own battery and instead receive external power through base 210 by way of power bus 245. If base 210 is not connected to external power source 218, then pod 212 will remain using the energy of its own battery until it reaches a "low power" state. Upon reaching the lower power state, pod 212 will request a power transfer from base 210 through cable 214. Upon the request, base 210 will transfer power through cable 214 unless base 210 has reached a low power state. If base 210 has reached a low power state, then base 210 will initiate an alarm informing the user that base 210 must be connected to external power source 218 or base 210 and pod 212 batteries must be replaced. It is contemplated there could be more than one tethered cable, such as one cable providing patient and/or pod data and another cable providing power without departing from the spirit of the invention. It is further contemplated the low power state for the base would be a power state above which a defibrillation therapy could successfully be provided to a patient. It is further contemplated that while the base and pod were both operating on battery power, if the base were to encounter a low power state on its batteries while the pod had not encountered a low power state on its battery that power could be shared from the pod battery to the base through power bus 245. It is further contemplated that the pod could be powered solely from the base through the availability of power on power bus 245 without pod battery 226 being present within the pod. It is further contemplated if the pod is remote from the base and communicating wirelessly and experienced a low power state, the pod would then sound an alarm and/or illuminate a visible indicator (e.g., LED or message on a display located on the pod) to the user informing the user the pod must be connected via the tethered cable or the pod must be docked so it can power share with the base. In an alternate embodiment, the low power state would be communicated wirelessly to the base whereby the base would sound an alarm and/or illuminate a visible indicator to the user informing the user the pod must be connected via the tethered cable or the pod must be docked so it can power share with the base. It is further contemplated that if the pod battery is easily replaced by the user, the low power state indication would prompt the user to replace the pod battery with a more full charged battery.

Generally, battery-charging control is maintained by a power module (not shown in FIG. 6) located in base 210. The power module is able to determine when a battery needs charging, how long the charging will take, and how much energy it will take to charge the battery. In the case of a regular "dumb" battery, the determination for these items can be made through examination of battery characteristics such as battery voltage, change in voltage, change in charge current drawn by the battery, and change in battery temperature. In an embodiment, the batteries in pod 212 and base 210 are "smart" batteries. The power module is able to communicate with smart batteries 222, 224, and 226 through communication multiplexer 240 and communication buses 230, 231, and 233 and provide the module with several variables providing the battery's status, such as energy level, whether the battery is in use presently, the battery's use over a time period, etc. It is of note pod 212 does not necessarily have to have a power module comparable to the power module in base 210. Instead of duplicating the circuitry of the power module in base 210, pod 212 contains power-multiplexing circuitry, which allows pod 212 to interrogate its smart battery and relay this information to the power module or it allows the pod's smart battery to directly communicate with the power module. The power module would then directly interrogate the pod's smart battery and retrieve the necessary information for charging. Further, the power module is isolated from the rest of the base circuitry so it can charge the batteries even when base 210 is turned off. This reduces the amount of circuitry needing power during the charging process, thus conserving energy and increasing circuit reliability for the circuitry that is not powered on during the charging process.

With reference again to FIG. 7, a schematic view of a defibrillator/monitor providing battery charging control of a patient module in an embodiment of the present invention is shown. When docked or connected by a tethered cable, base 220 establishes several connections to pod 228 through communication bus 230, battery charging bus 246, and power bus 245. Power bus 245 provides power to pod 228 through base 220 when base 220 is connected to an external power source or when pod 228 is in a "low power" state. In the present embodiment, base 220 is able to control the charging of batteries 222, 224, and 226 located within pod 228. As discussed above, communication bus 230 and charging bus 246 allow base 220 to charge batteries 222, 224, and 226 and thus allows for only one power module 232 (similar to power module 86), which remains in base 220, thus reducing the amount of circuitry needed. If base 220 is connected to an external power source, power is transferred to base 220 through battery lines 234 and 236 via an external or internal power supply. Power microprocessor 238 is continually interrogating batteries 222, 224, and 226 through communication multiplexer 240, to obtain vital battery information such as voltage and current parameters, battery's charge level, and a battery serial number. Microprocessor 238 then determines, which two of three batteries 222, 224, and 226 requiring charging based upon the interrogated battery information. Since base 220 has two independent power lines 234 and 236, base 220 is able to charge two of the three batteries 222, 224, and 226 simultaneously. For example, module 232 could charge batteries 222 and 224, or 222 and 226, or 224 and 226 at the same time. Generally, batteries 222 and 224 are charged first so base 220 is quickly provided with the energy to provide defibrillation therapy. It is further contemplated any one of batteries 222, 224, and 226 could be charged by themselves. It is further contemplated all three batteries 222, 224, and 226 could be charged together without departing from the spirit of the invention.

Once processor 238 determines which two batteries need charging, power is routed through a switching matrix comprised of switches 242 and 244 to batteries 222 or 224 or through battery charger bus 246 to battery 226. Processor 238 controls which batteries will be charged through power multiplexer 239, which controls the switching matrix. Once a battery is fully charged, processor 238 then routes the power to the third and remaining battery in need of charging. When batteries 222, 224, and 226 are all fully charged, switches 242 and 244 are opened and the incoming power continues to power base 220 and pod 228 through power bus 245. It is further contemplated that switches 242 and 244 would not be needed if the battery charging power provided through battery charger buses 234 and 236 were to be placed in an "off power" state that would not significantly load the batteries 242 and 244 when charging power is not needed.

When pod 228 is being used in a wireless mode, communication bus 248 is engaged by power processor 249 to route battery 226 information via signal processor 250. Once the power processor 249 routes the information to signal processor 250, the signal processor 250 processes the battery information and transmits all battery 226 information to base 220. It is fully contemplated processors 238 and 249 could be any type of processor including a microcontroller or an ASIC (Application Specific Integrated Circuit) without departing from the spirit of the invention. Further, signal processor 250 can be any type of signal processor known to those with skill in the art. Base 220 uses the battery information to monitor the charge on battery 226 and displays this information on a monitor (not shown) as a fuel gauge, which is discussed in more detail below, so the user can easily monitor the status of the pod's battery 226. Base 220 also uses this information to initiate an alarm on base 220 and/or pod 228 to alert the user the pod's battery 226 is depleted and pod 228 needs to be connected via a cable to base 220 or pod 228 needs to be docked with base 220 so battery 226 can be charged. Generally, pod 228 is turned off when it is charging. However buses 246 and 230 remain open so pod 228 battery 226 can be recharged and be interrogated by base 220 to monitor the charging process. It is further contemplated that pod battery charging can occur when the pod is operating and is powered by the base power through power bus 245.

With reference once again to FIG. 7, in an another embodiment there is a power on and power off interaction between base 220 and pod 228. If base 220 and pod 228 are in electrical contact either through a tethered cable or through pod 228 being docked with base 220, a user could press an on/off button (not shown) on base 220 powering up base 220 and a signal would be sent from system control module 300 on system bus 302 to pod 228 instructing pod 228 to power up. If the user then desired to power down base 220, they would then press the on/off button on base 220 powering down base 220 and a signal would be sent from system control module 300 on system bus 302 to pod 228 instructing pod 228 to power down. In an alternative embodiment, pod 228 would be able to detect base 220 had powered up by power being transferred across bus 245 and then pod 228 would power up itself. Upon power up of base 220, system control module 300 establishes the initial condition of base 220 and pod 228 and coordinates communication of all modules. The control module 300 then confirms with processor 250 through control bus 302 the pod's power situation (e.g., pod 228 is running off battery 226 or is receiving power from base 220 through power bus 245) and the pod's current power management.

Similar to base 220, pod 228 has an on/off button 225 where a user can press the button and turn pod 228 on or off. If pod 228 is docked with base 220 and pod 228 is powered up, pod 228 will begin to interrogate communications with base 220. If, after a period of minutes, pod 228 cannot establish communications with base 220, then pod 228 would assume powering up was inadvertent and turn itself off to conserve battery power. In another embodiment, the user would be able to power up base 220 from pod 228 similar to powering up pod 228 from base 220 discussed above. Pod 228 can also be powered up from base 220 in a wireless mode. If pod 228 is remote from base 220 and a user powers up base 220, base 220 will determine pod 228 is not directly connected to base 220 and then transmit an RF signature which when received by pod 228 would power up pod 228. In addition, pod 228 could be powered down from base 220 as long as pod 228 is within transmitting range of base 220. If communications between pod 228 and base 220 is lost, pod 228 will try to reestablish communications for a pre-determined amount of time. If pod 228 is unable to reestablish communications with base 220, then pod 228 will power itself down to conserve battery power. However, if pod 228 came back within communication range of base 220, then the RF signature from base 220 would power up pod 228 and base 220 would begin reestablishing communications. It is further contemplated that the pod and base could swap roles in the previously described wireless on/off descriptions without departing from the spirit of the invention.

With reference to FIG. 8, a schematic view of a defibrillator/monitor battery-charging scheme in an embodiment of the present invention is shown. External adapter 262 provides battery-charging circuitry for charging batteries 264 and 266 located within base 260. External adapter 262 can be a docking station or an adaptor. In this embodiment, the battery charging circuitry has been removed from base 260 to reduce the cost of base 262 and to make base 262 lighter. External adapter 262 can receive power input from an AC source 268 or a DC source 270 or both; however, both are not necessarily needed together to stay within the spirit of the invention. If AC source 268 is utilized, the power is first filtered through AC filter 272 and then converted to 10-16V DC by converter 274. This voltage can then be routed to power module 276 where it is used to power base 260 and routed to boost converter 280, which converts the power to 20V which is provided to battery charging circuits 282 and 284. If DC source 270 is utilized, the power is filtered by DC filter 278 and routed to power module 276 where it is used to power base 260 and boost converter 280 which converts the power to 20V which is provided to battery charging circuits 282 and 284.

Communications bus 285 provides communication with power processor 286, a pod battery (not shown) through multiplexer 288. Bus 285 further provides communication with power processor 286 and battery chargers 282 and 284 through bus multiplexer 290. Generally, bus 285 is an Inter-IC bus, however, it is fully contemplated bus 285 could be any type of bus know to those with skill in the art without departing from the spirit of the invention. Through communication bus 285 power processor 286 provides chargers 282 and 284 with the proper charging parameters, such as proper voltage, current, and charge time, based upon information interrogated from batteries 264 and 266. Battery chargers 282 and 284 then use this charging parameter information to provide the correct charging voltage and current to power module 276, which then routes this power to batteries 264 and 266 through battery circuit boards 292 and 294. Therefore bus 285 allows processor 286 to parametrically control the charging of batteries 282 and 284. This allows for the use of varying types of batteries as well as algorithms, which might change over time due to technology changes. It is further contemplated that the distribution of battery charging, power control, and power switching functions could be redistributed among the docking station, base, and pod without departing from the spirit of the invention. It is further contemplated that the power and battery charging buses could be combined into a single bus without departing from the spirit of the invention. It is further contemplated that the power on/off control signal 302 between the base 220 and pod 228 and communication bus 230 can be combined into a single bus without departing from the spirit of the invention. It is further contemplated that the power and communication buses could be combined into a single bus without departing from the spirit of the invention. In an alternate embodiment, the smart battery information could be communicated from the pod battery 226 to the pod power controller 249 and then communicated to the base power processor 238 via the communication bus 230.

Thus, embodiments of the AN EXTERNAL DEFIBRILLATOR WITH POWER AND BATTERY SHARING CAPABILITIES WITH A POD are disclosed. One skilled in the art will appreciate that the present teachings can be practiced with embodiments other than those disclosed. The disclosed embodiments are presented for purposes of illustration and not limitation, and the present teachings are limited only by the claims that follow.

What is claimed is:

1. A modular external defibrillator system, comprising:
    a portable base containing a base battery and a defibrillator module configured to deliver a defibrillation shock to a patient;
    a patient parameter monitoring pod including a pod battery, the pod configured to connect to a patient via lead cables and to receive patient data via the lead cables, the patient data including at least one patient vital sign, and the pod is operable to collect patient data without receiving power from the portable base; and
    a power supply sharing link between the portable base and the pod, wherein the portable base includes a power module configured to determine a pod battery charge condition and a base battery charge condition, and the portable base is configured to selectively charge the pod battery via the power supply sharing link based on the pod battery charge condition and the base battery charge condition.

2. The defibrillator system of claim 1, wherein the portable base is configured to selectively charge the pod battery in response to the power module determining the pod battery charge condition is a low charge condition.

3. The defibrillator system of claim 1, wherein the portable base charges the pod battery when the portable base is connected to an external power source.

4. The defibrillator system of claim 1, wherein the base battery is configured to selectively charge the pod battery.

5. The defibrillator system of claim 1, wherein the portable base is configured to provide energy to operate the defibrillator module to deliver the defibrillation shock to the patient when the portable base is unconnected to an external energy source.

6. The defibrillator system of claim 1, wherein the portable base includes a power module, and the power module of the portable base is configured to power the pod battery when the portable base is turned off.

7. The defibrillator system of claim 1, wherein the portable base is configured to not initiate charging of the pod battery in response to the power module determining the pod battery charge is not in a low condition.

8. A modular external defibrillator system, comprising:
    a portable base containing a base battery and a defibrillator module configured to deliver a defibrillation shock to a patient;
    a patient parameter monitoring pod including a pod battery, the pod configured to connect to a patient with patient lead cables and to receive patient data via the patient lead cables, the patient data including at least one patient vital sign, and the pod is configured to receive patient data while receiving power from the portable base; and
    a power supply sharing link between the portable base and the pod;
    wherein the portable base includes a power module configured to determine a pod battery charge condition and a base battery charge condition and is configured to selectively power the pod battery via the power supply sharing link based on the pod battery charge condition and the base battery charge condition.

9. The defibrillator system of claim 8, wherein the portable base selectively charges the pod battery in response to the power module determining the pod battery as being in a low charge condition.

10. The defibrillator system of claim 8, wherein the portable base powers the pod when the portable base is connected to an external power source.

11. The defibrillator system of claim 8, wherein the base battery is configured to power the pod.

12. The defibrillator system of claim 8, wherein the portable base is configured to not initiate charging of the pod battery in response to the power module determining the pod battery charge is not in a low condition.

13. A modular external defibrillator system, comprising:
    a portable base containing a defibrillator module configured to deliver a defibrillation shock to a patient;
    a patient parameter monitoring pod including a pod battery, the pod configured to connect to a patient with patient lead cables and to receive patient data via the patient lead cables, the patient data including at least one patient vital sign; and
    a wired connection power communications link between the portable base and the pod,
    wherein the portable base includes a power module configured to determine a patient parameter monitoring pod battery charge condition and a portable base battery charge condition and is configured to selectively power the pod battery via the power communications link based on the pod battery charge condition and the base battery charge condition, wherein the pod is configured to receive power-on command signaling from the portable base via the power communications link and power-on in response to the power-on command signaling, wherein the pod is further operable to power-on without receiving the power-on command signaling, wherein the pod is operable to power-on to a state where the pod may collect patient data, and wherein the pod is operable to power down to conserve power after receiving no signal from the portable base for a predetermined amount of time.

14. The modular external defibrillator system of claim 13, wherein the power-on command signaling is communicated via the presence of a power supply over the power communications link.

15. The modular external defibrillator system of claim 13, wherein the pod is operable to return to a power off condition in response to receiving a signal over the power communications link.

* * * * *